US012722023B1

(12) United States Patent
Zeng

(10) Patent No.: US 12,722,023 B1
(45) Date of Patent: Sep. 1, 2026

(54) INFRARED MASSAGE HEAD

(71) Applicant: Shenzhen Laige Technology Co., Ltd., Shenzhen (CN)

(72) Inventor: Feng Zeng, Shenzhen (CN)

(73) Assignee: Shenzhen Laige Technology Co., Ltd., Shenzhen (CN)

( * ) Notice: Subject to any disclaimer, the term of this patent is extended or adjusted under 35 U.S.C. 154(b) by 0 days.

(21) Appl. No.: 19/446,908

(22) Filed: Jan. 12, 2026

(30) Foreign Application Priority Data

Nov. 6, 2025 (CN) ........................ 202522362294.9

(51) Int. Cl.
*A61N 5/06* (2006.01)
*A61F 7/00* (2006.01)
*A61H 23/00* (2006.01)
*A61N 5/00* (2006.01)

(52) U.S. Cl.
CPC ............ *A61N 5/0613* (2013.01); *A61F 7/007* (2013.01); *A61H 23/006* (2013.01); *A61F 2007/0075* (2013.01); *A61F 2007/0087* (2013.01); *A61F 2007/0093* (2013.01); *A61H 2201/0153* (2013.01); *A61H 2201/0207* (2013.01); *A61H 2201/0285* (2013.01); *A61H 2201/10* (2013.01); *A61H 2201/503* (2013.01); *A61N 2005/005* (2013.01); *A61N 2005/0626* (2013.01); *A61N 2005/0644* (2013.01); *A61N 2005/065* (2013.01); *A61N 2005/0659* (2013.01); *A61N 2005/0663* (2013.01)

(58) Field of Classification Search
CPC ......... A61N 5/0613; A61F 7/00; A61F 7/007; A61F 2007/0075; A61F 2007/0087; A61F 2007/0093; A61H 23/00; A61H 23/006; A61H 2201/0153; A61H 2201/0207; A61H 2201/0285; A61H 2201/10; A61H 2201/503; A61H 2005/0644; A61H 2005/065; A61H 2005/0659; A61H 2005/0663
USPC ........................................................... 600/15
See application file for complete search history.

(56) References Cited

U.S. PATENT DOCUMENTS

2006/0211961 A1* 9/2006 Meyer .................... A61H 7/005 601/72
2010/0274162 A1* 10/2010 Evans ................ A61H 15/0092 601/46

(Continued)

*Primary Examiner* — Rachel T Sippel
*Assistant Examiner* — Gwynneth L Howell

(57) ABSTRACT

An infrared massage head includes a mounting shell, a light-transmitting shell, a heat-conducting contact member, a thermoelectric unit, and an infrared light module. At least a portion of the light-transmitting shell is light-transmissive, the light-transmitting shell is mounted to the mounting shell, the light-transmitting shell and the mounting shell cooperatively form a mounting cavity, and the light-transmitting shell is arranged with a first contact face. The heat-conducting contact member is mounted to the light-transmitting shell or the mounting shell, and at least a portion of the heat-conducting contact member is exposed from the first contact face and has a second contact face. The thermoelectric unit is configured to conduct heat to the heat-conducting contact member. The infrared light module is located in the mounting cavity, and light emitted by the infrared light module is capable of pass through the light-transmitting shell.

12 Claims, 6 Drawing Sheets

(56) References Cited

U.S. PATENT DOCUMENTS

2014/0336541 A1* 11/2014 Tsao .......................... A61N 7/02
601/3
2015/0305969 A1* 10/2015 Giraud .................. A61H 7/005
601/84
2022/0032082 A1* 2/2022 Shenfarber .......... A61K 8/9789
2022/0040030 A1* 2/2022 Tang ........................ A61H 7/00
2022/0168175 A1* 6/2022 Tang ........................ H01B 7/22
2022/0233399 A1* 7/2022 Wersland ........... A61H 23/0254
2022/0362052 A1* 11/2022 Hart ........................ A61F 7/007
2023/0218479 A1* 7/2023 Hu ......................... A61H 23/00
601/84
2023/0390555 A1* 12/2023 Stavale .................. A61H 7/005
2024/0374468 A1* 11/2024 Carden ................ A61H 23/006
2025/0099323 A1* 3/2025 Zhou .................... A61H 23/006
2025/0366594 A1* 12/2025 Dijkstra ............... A45D 34/042

* cited by examiner

INFRARED MASSAGE HEAD

CROSS REFERENCE TO RELATED APPLICATIONS

This application claims priority of the Chinese patent application No. 202522362294.9, filed on Nov. 6, 2025, the disclosure of which is hereby incorporated by reference in its entirety.

FIELD OF THE DISCLOSURE

The present disclosure relates to the technical field of massage devices, in particular to an infrared massage head.

BACKGROUND

As people's quality of life continuously improves, people pay more and more attention to their physical health. After long hours of work, many people use massage devices to massage various parts of the body, so that the user's tense body can be relaxed, improving the user's living state and quality of life.

For example, existing fascia guns can be used for muscle relaxation. Fascia guns generally use massage heads to vibrate the user's skin, thereby achieving effects such as reducing local tissue tension, relieving pain, and promoting blood circulation. However, existing massage heads have single functions, usually only used for vibrating human skin or for simple heating, resulting in insufficient therapeutic effects.

SUMMARY

The following presents a simplified summary of the disclosure in order to provide a basic understanding of some aspects of the disclosure. This summary is not an extensive overview of the disclosure. It is not intended to identify critical elements or to delineate the scope of the disclosure. Its sole purpose is to present some concepts of the disclosure in a simplified form as a prelude to the more detailed description that is presented elsewhere.

In some embodiments, an infrared massage head is provided. The infrared massage head includes a mounting shell, a light-transmitting shell, a heat-conducting contact member, a thermoelectric unit, and an infrared light module. At least a portion of the light-transmitting shell is light-transmissive, the light-transmitting shell is mounted to the mounting shell, the light-transmitting shell and the mounting shell cooperatively form a mounting cavity, and the light-transmitting shell is arranged with a first contact face on a side of the light-transmitting shell facing away from the mounting shell. The heat-conducting contact member is mounted to the light-transmitting shell or the mounting shell, and at least a portion of the heat-conducting contact member is exposed from the first contact face and has a second contact face. The thermoelectric unit is configured to conduct heat to the heat-conducting contact member. The infrared light module is located in the mounting cavity, and light emitted by the infrared light module is capable of pass through the light-transmitting shell.

BRIEF DESCRIPTION OF THE DRAWINGS

Illustrative embodiments of the present disclosure are described in detail below with reference to the attached drawing figures.

Numeral reference in the drawings.

Figure 1:
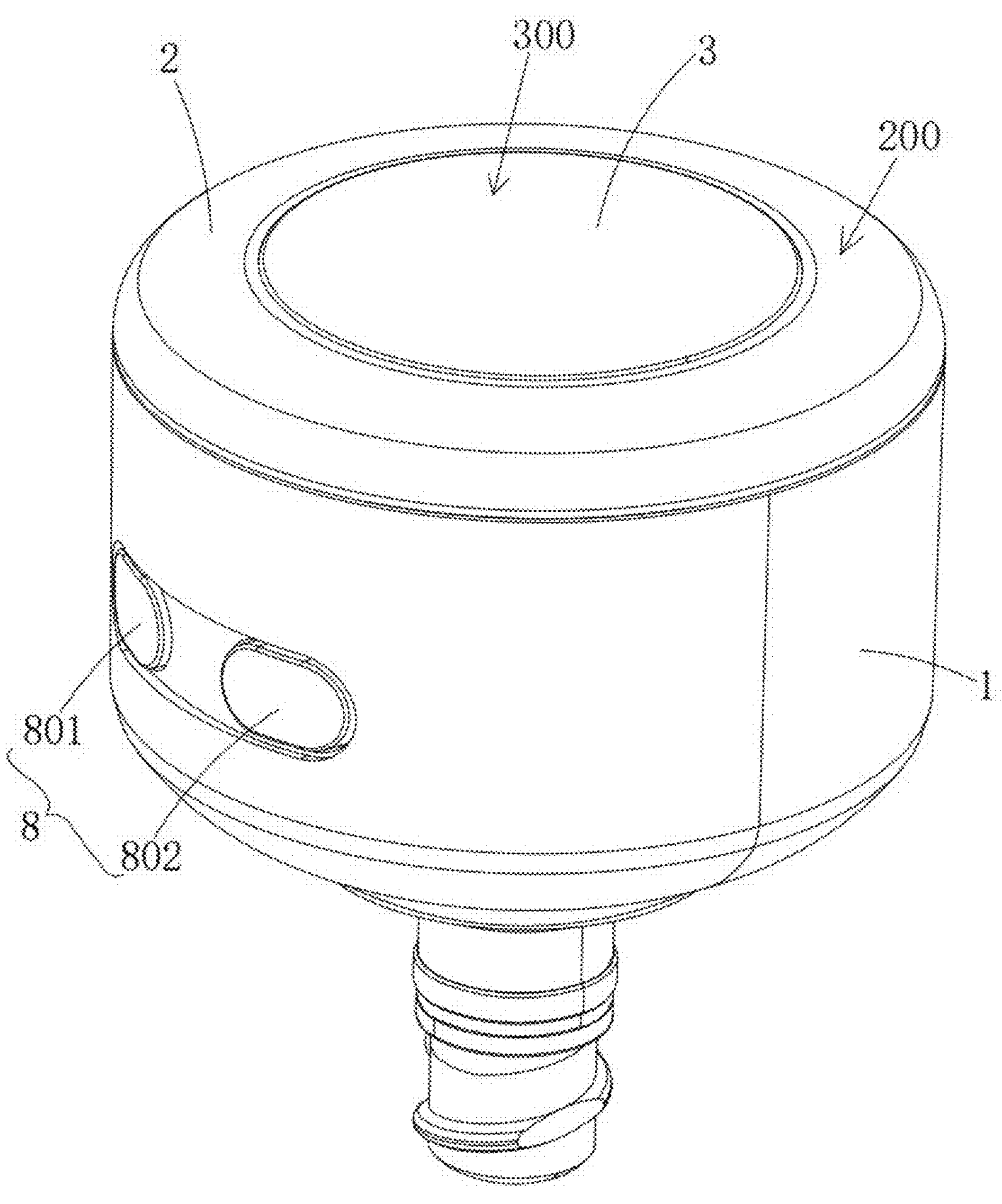
FIG. 1 is a schematic view of an overall structure of an infrared message head according to an embodiment of the present disclosure.

- 1—mounting shell; 120—mounting cavity;
- 2—light-transmitting shell; 200—first contact face; 201—connecting gap; 21—light-transmitting portion; 22—bearing bracket; 23—fixing portion; 210—mounting hole;
- 3—heat-conducting contact member; 300—second contact face; 31—contact portion; 32—connecting portion;
- 4—thermoelectric unit;
- 5—infrared light module; 51—light board; 52—light bead; 521—red light unit; 522—near-infrared light unit;
- 6—control board;
- 7—battery;
- 8—control button; 801—first control key; 802—second control key.

DETAILED DESCRIPTION

The following describes some non-limiting exemplary embodiments of the disclosure with reference to the accompanying drawings. The described embodiments are merely a part rather than all of the embodiments of the disclosure. All other embodiments obtained by a person of ordinary skill in the art based on the embodiments of the disclosure shall fall within the scope of the disclosure.

Unless otherwise defined, all technical and scientific terms used herein have the same meaning as commonly understood by those skilled in the art to which the present disclosure belongs. The terms used in the description of the present disclosure herein are intended for describing particular embodiments only and are not intended to limit the present disclosure. In the description, claims, and the above drawings of the present disclosure, the terms "including" and "having", as well as their variants, are intended to convey a non-exclusive inclusion. The terms "first", "second", etc., as used herein, are intended to distinguish between different objects, rather than to describe a particular order.

Reference to "embodiments" herein implies that a particular feature, structure, or characteristic described in conjunction with an embodiment may be included in at least one embodiment of the present disclosure. The appearance of the phrase at various places in the specification does not necessarily refer to the same embodiment, nor is it a separate or an alternative embodiment that is mutually exclusive of other embodiments. One skilled in the art would explicitly and implicitly understand that the embodiments described herein can be combined with other embodiments.

Referring to FIGS. 1 to 6, the present disclosure provides an infrared massage head, including a mounting shell 1, a light-transmitting shell 2, a heat-conducting contact member 3, a thermoelectric unit 4, and an infrared light module 5.

As shown in FIG. 1, the light-transmitting shell 2 may be mounted to the mounting shell 1, and at least a portion of the light-transmitting shell 2 may be light-transmissive. The light-transmitting shell 2 and the mounting shell 1 cooperatively define a mounting cavity 120. The light-transmitting shell 2 may have a first contact face 200 on a side of the light-transmitting shell 2 facing away from the mounting shell 1. The heat-conducting contact member 3 may be mounted to the light-transmitting shell 2 or the mounting shell 1, and at least a portion of the heat-conducting contact member 3 may be arranged to be exposed from the first contact face 200, and the portion of the heat-conducting contact member 3 exposed from the first contact face 200 may have a second contact face 300. The first contact face 200 and the second contact face 300 may be both used for contacting human skin, i.e., the first contact face 200 and second contact face 300 may be actual contact areas between the user and the massage head.

The thermoelectric unit 4 may be attached to a side of the heat-conducting contact member 3 facing away from the second contact face 300, so that the thermoelectric unit 4 may transfer heat to the heat-conducting contact member 3 more efficiently, thereby causing a temperature of the heat-conducting contact member 3 to change more rapidly.

The infrared light module 5 may be arranged in the mounting cavity 120, and light emitted by the infrared light module 5 may pass through the light-transmitting shell 2.

After the infrared massage head is mounted to a fascia gun, it can not only perform vibration massage but also use the thermoelectric unit 4 and a metal contact face to perform cold/hot compress therapy on human skin, as well as use infrared light to reach subcutaneous tissue of human body to promote blood circulation, improve blood flow, reduce oxidative stress, and promote tissue repair and regeneration. Therefore, the infrared massage head may perform therapy from multiple aspects, resulting in better therapeutic effects.

Regarding a connection structure between the mounting shell 1 and the light-transmitting shell 2, in some embodiments, specifically, the light-transmitting shell 2 may be mounted to the mounting shell 1 in a snap-fit manner, or the light-transmitting shell 2 may be adhesively bonded to the mounting shell 1, or by other means. The light-transmitting shell 2, the mounting shell 1, and the heat-conducting contact member 3 may cooperatively seal the mounting cavity 120 to prevent water from entering the mounting cavity 120 and damaging electrical components.

Figure 2:
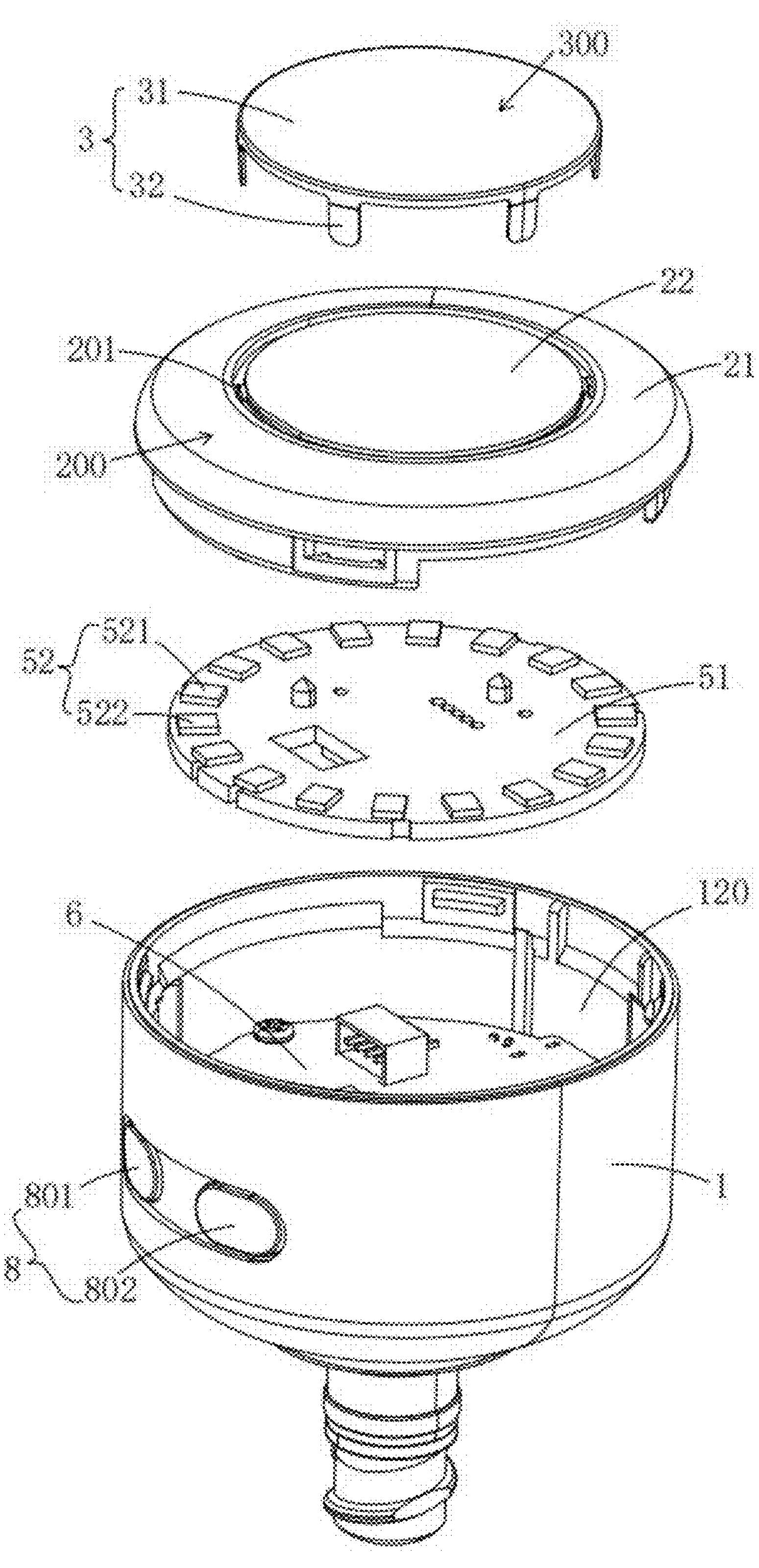
FIG. 2 is an exploded view of the infrared message head according to an embodiment of the present disclosure.

Regarding a connection structure between the heat-conducting contact member 3 and the light-transmitting shell 2, referring to FIGS. 2 to 5, in some embodiments, a connecting gap 201 may be formed on the light-transmitting shell 2. The heat-conducting contact member 3 may include a contact portion 31 and a connecting portion 32 formed on the contact portion 31. The contact portion 31 may be arranged on an outer side of the light-transmitting shell 2, and a side of the contact portion 31 facing away from the light-transmitting shell 2 may be the second contact face 300, i.e., a top face of the contact portion 31 as shown in FIG. 2 may be the second contact face 300. The second contact face 300 may be a circular plane or other shape adapted to the skin.

The connecting portion 32 may pass through the connecting gap 201 and may be bendably arranged to enable the heat-conducting contact member 3 and the light-transmitting shell 2 to be fixed relative to each other. Specifically, a plurality of connecting portions 32 may be provided, for example, 2 to 6. The connecting portions 32 may extend from an edge of the contact portion 31. Each of the contact portion 31 and the connecting portions 32 may be made of a metal material which may have a high thermal conductivity and allow the connecting portions 32 to be bent. After the connecting portion 32 passes from top to bottom through the connecting gap 201 on the light-transmitting shell 2 and extends into the mounting cavity 120, the connecting portion 32 may be bent and pressed against an inner side of the light-transmitting shell 2 to fix the contact portion 31 onto the light-transmitting shell 2 via an elastic pressing force of the connecting portion 32.

In some embodiments, the thermoelectric unit 4 may be a thermoelectric semiconductor sheet, which may be sandwiched between the contact portion 31 and the light-transmitting shell 2. Specifically, the thermoelectric semiconductor sheet may be attached to a back face of the contact portion 31. By controlling a current direction of the thermoelectric unit 4, the heat-conducting contact member 3 may be heated (corresponding to hot compress) or cooled (corresponding to cold compress). Due to the high thermal conductivity of metal, the heat or cold may be quickly transferred to the second contact face 300, and then from the second contact face 300 to the user's skin, achieving rapid temperature response. In other embodiments, the thermoelectric unit 4 may also be an electric heating wire, electric heating plate, etc.

An outer wall of the mounting shell 1 may be roughly cylindrical in shape. Correspondingly, the light-transmitting shell 2 may be also roughly circular in shape, and the contact portion 31 mounted on the light-transmitting shell 2 may be also circularly arranged to reduce presence of sharp edges, preventing excessive local pressure on the user which may affect the user experience. Additionally, the heat-conducting contact member 3 may include the plurality of connecting portions 32 distributed around a circumference of the contact portion 31. A plurality of connecting gaps 201 may be formed on the light-transmitting shell 2 corresponding to the plurality of connecting portions 32. The plurality of connecting portions 32 and the contact portion 31 cooperatively clamp onto the light-transmitting shell 2.

Regarding a connection structure between the infrared light module 5 and the light-transmitting shell 2, referring to FIG. 2, in some embodiments, the infrared light module 5 may include a light board 51 and a plurality of light beads 52 annularly distributed on the light board 51. The light-transmitting shell 2 may include a light-transmitting portion 21 and a bearing bracket 22. The light-transmitting portion 21 may be annular and define a mounting hole 210. The bearing bracket 22 may be arranged in the mounting hole 210, and the bearing bracket 22 and an inner wall of the light-transmitting portion 21, which defines the mounting hole 210, may cooperatively define the aforementioned plurality of connecting gaps 201. The light board 51 may be fixed in the mounting cavity 120 and arranged such that the light beads 52 correspond to the light-transmitting portion 21. The bearing bracket 22 may be used for mounting the thermoelectric unit 4 and the heat-conducting contact member 3. In some embodiments, the bearing bracket 22 and the light-transmitting portion 21 may be integrally formed as a one-piece structure.

The light board 51 may be a circuit board, and the infrared light module 5 may be actually a circuit board integrated with a plurality of light beads 52. The light board 51 may be fixedly mounted to the bearing bracket 22 via bolts, or directly fixed to an inner wall of the mounting cavity 120 (for example, fixed to the mounting shell 1). The light beads 52 may emit infrared light toward the light-transmitting portion 21, so that the infrared light may pass through the light-transmitting shell 2 and irradiate the user's skin. An annular distribution of the plurality of light beads 52 may make the infrared light emitted by the massage head more uniformly distributed.

Figure 6:
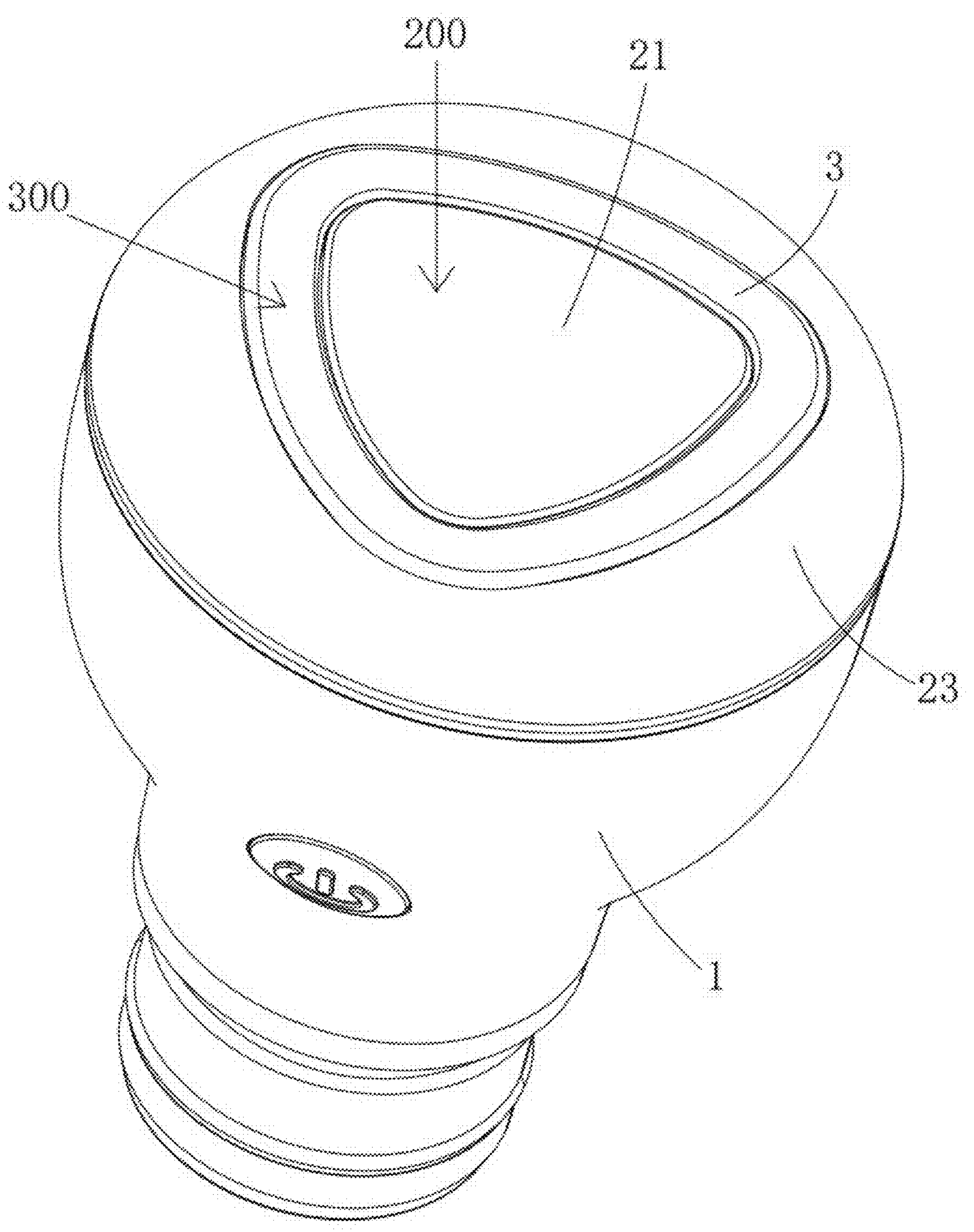
FIG. 6 is a schematic view of the overall structure of the infrared message head according to another embodiment of the present disclosure, with the heat-conducting contact member surrounding a light-transmitting portion.

Regarding the connection structure between the infrared light module 5 and the light-transmitting shell 2, referring to FIG. 6, in other embodiments, the infrared light module 5 may include a light board 51 and a plurality of light beads 52 distributed on the light board 51. The light-transmitting shell 2 may include a light-transmitting portion 21 and a fixing portion 23. The fixing portion 23 may be mounted to the mounting shell 1 and connected to the light-transmitting portion 21, such that the light-transmitting portion 21 may be located at a central portion of the infrared massage head. The fixing portion 23 may be arranged to surround the circumference of the light-transmitting portion 21, and the fixing portion 23 and the light-transmitting portion 21 may cooperatively define the plurality of the aforementioned connecting gaps 201. The light board 51 may be fixed in the mounting cavity 120 and the light beads 52 may be arranged corresponding to the light-transmitting portion 21. The thermoelectric unit 4 and the heat-conducting contact member 3 may be both fixedly mounted to the fixing portion 23, and the heat-conducting contact member 3 may be annularly arranged to surround the light-transmitting portion 21. The fixing portion 23 and the light-transmitting portion 21 may be integrally formed as a one-piece structure. The first contact face 200 may be roughly triangular in shape, and the second contact face 300 may be roughly a hollow triangular ring.

In some embodiments, the light-transmitting portion 21 may be made of a black translucent material, such as black PC plastic, which may both filter stray light to avoid dazzling and ensure a transmittance of infrared light. Furthermore, the infrared light module 5 may include a red light unit 521 and a near-infrared light unit 522, i.e., the plurality of light beads 52 include red light beads 52 and near-infrared light beads 52. The red light beads 52 may emit visible light with a wavelength of 600-700 nm, acting on an epidermal layer. The near-infrared light beads 52 may emit invisible near-infrared light with a wavelength of 800-1000 nm, used to reach deep muscles, achieving a layered therapeutic effect through combined irradiation. A presence of red visible light may allow users to both feel the heat and see the red light, thereby trusting the therapeutic effect of the infrared rays. In other embodiments, the light-transmitting portion 21 may also be made of other colored translucent materials.

Figure 3:
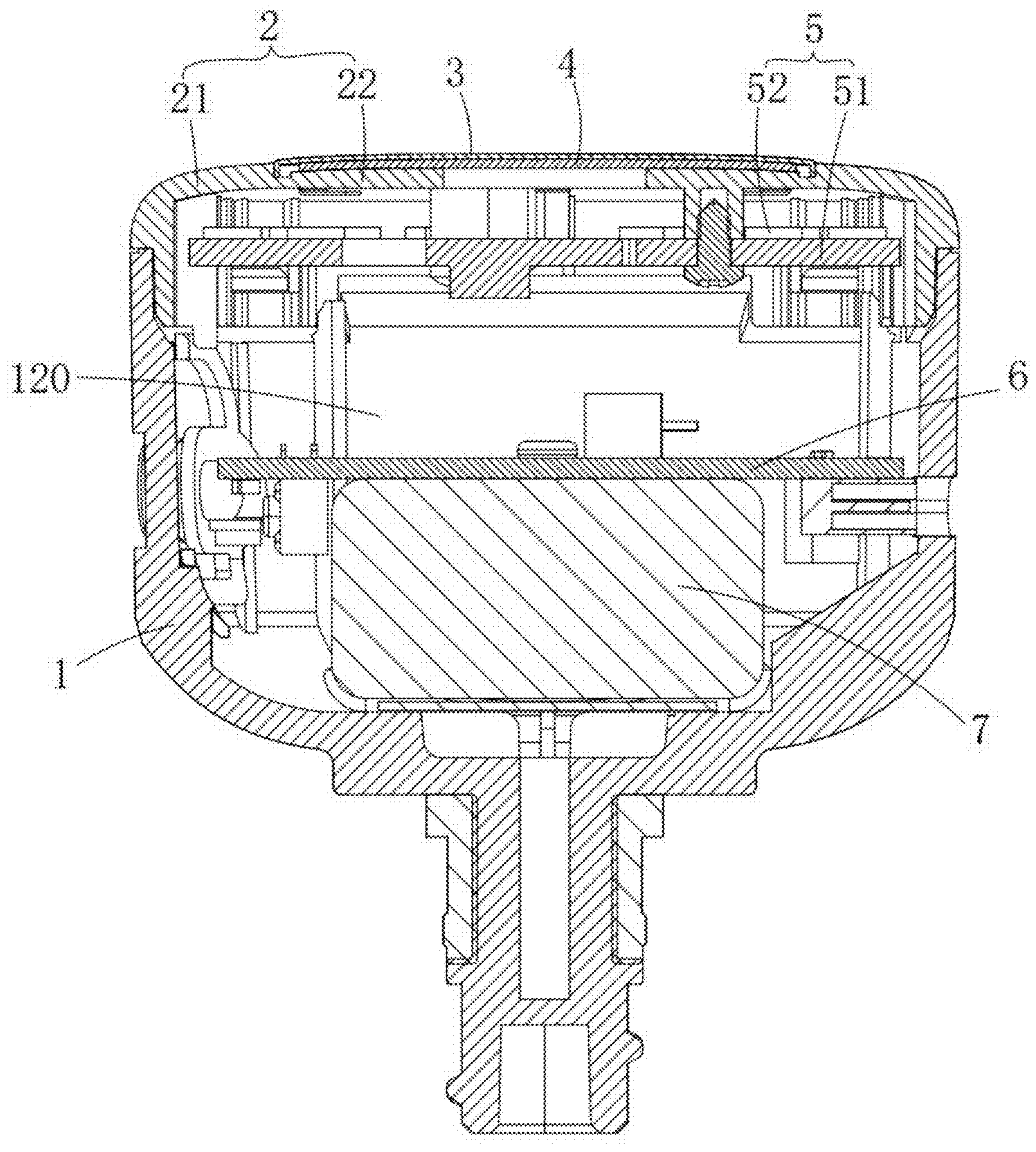
FIG. 3 is a cross-sectional view of the infrared message head according to an embodiment of the present disclosure.
Figure 4:
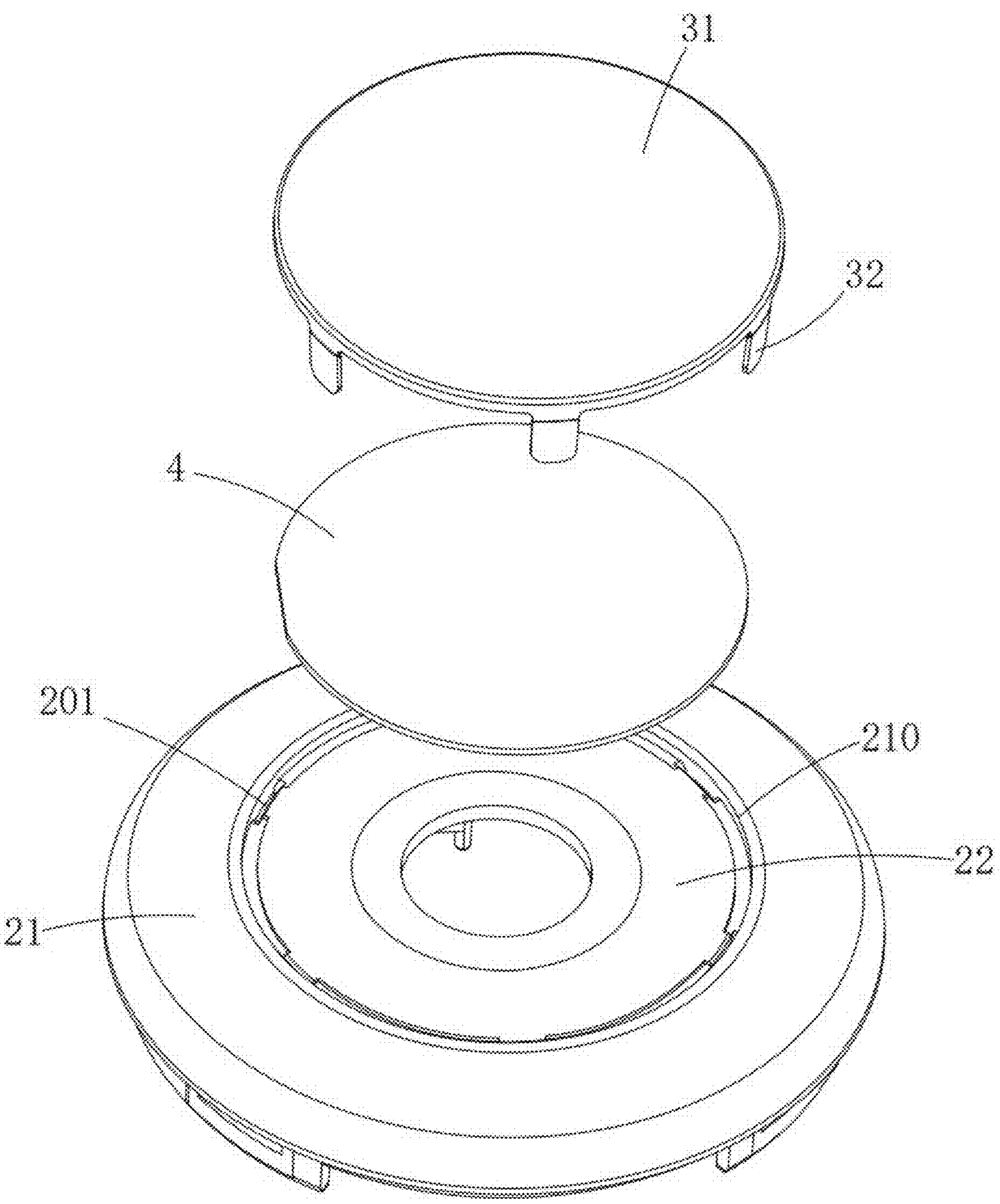
FIG. 4 is a schematic view of a connection structure between a light-transmitting shell, a heat-conducting contact member, and a thermoelectric unit according to an embodiment of the present disclosure.
Figure 5:
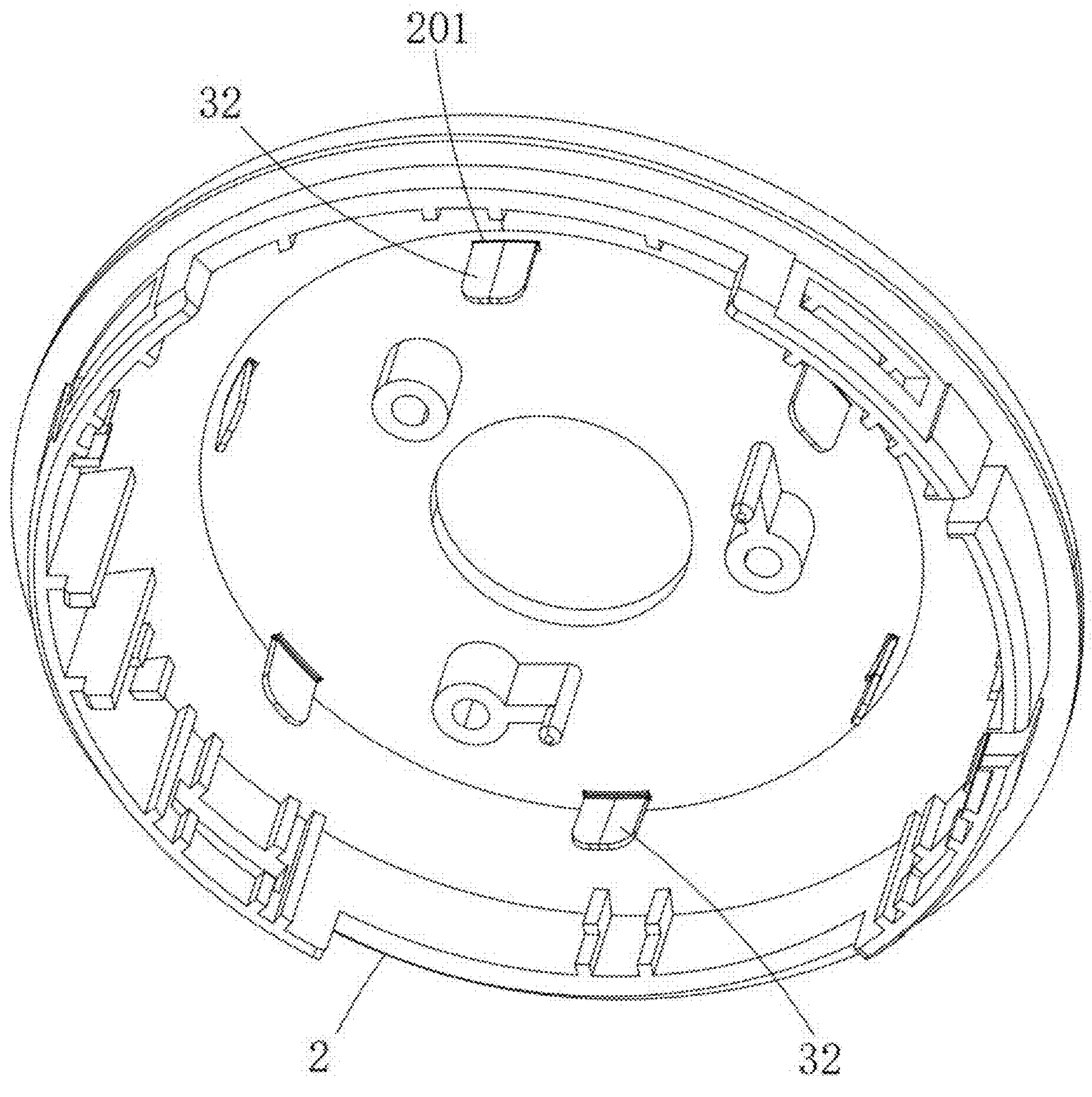
FIG. 5 is a schematic view of a connection structure between the light-transmitting shell and the heat-conducting contact member according to an embodiment of the present disclosure.

In some embodiments, referring to FIGS. 2 and 3, the infrared massage head may further include a control board 6, a battery 7, a charging module, and a control button 8. The control board 6 and the battery 7 may be both arranged in the mounting cavity 120 and may be both fixed to the mounting shell 1. A portion of the control button 8 may be exposed outside the mounting shell 1. The control board 6 may be electrically connected to the battery 7, the control button 8, the charging module, the thermoelectric unit 4, and the infrared light module 5. A charging hole may be formed on the mounting shell 1, corresponding to the charging module, so that a charging cable may be electrically connected to the charging module through the charging hole.

Specifically, the control board 6 may be a PCBA circuit board. A working state of the thermoelectric unit 4 or the infrared light module 5 may be controlled via the control button 8 to meet different therapeutic needs. For example, as shown in FIG. 1, the control button 8 may include a first control key 801 and a second control key 802. The first control key 801 may be associated with the thermoelectric unit 4, and the second control key 802 may be associated with the infrared light module 5. A power and heat level of the thermoelectric unit 4 may be adjusted via the first control key 801, and a brightness/on-off state of the infrared light may be adjusted via the second control key 802, thereby achieving multifunctional combined therapy effects, such as "hot compress+near-infrared light", "cold compress+red light", or others.

In some embodiments, to make an effect of the control button 8 clearer to the user, indicator lights may be respectively arranged inside the first control key 801 and the second control key 802. After pressing the first control key 801 or the second control key 802, brightness and color of the indicator lights inside may be different. The user may distinguish the effect based on changes in the indicator lights.

It should be noted that the infrared massage head may be not limited to use on fascia guns, and may also be used on any other devices requiring a massage head.

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure.

It will be understood that certain features and subcombinations are of utility and may be employed without reference to other features and subcombinations and are contemplated within the scope of the claims. Unless indicated otherwise, not all steps listed in the various figures need be carried out in the specific order described.

The invention claimed is:

1. An infrared massage head, comprising:

a mounting shell;

a light-transmitting shell, wherein at least a portion of the light-transmitting shell is light-transmissive, the light-transmitting shell is mounted to the mounting shell, the light-transmitting shell and the mounting shell cooperatively form a mounting cavity, and the light-transmitting shell is arranged with a first contact face on a side of the light-transmitting shell facing away from the mounting shell;

a heat-conducting contact member, mounted to the light-transmitting shell or the mounting shell, wherein at least a portion of the heat-conducting contact member is exposed from the first contact face and has a second contact face;

a thermoelectric unit, configured to conduct heat to the heat-conducting contact member; and an infrared light module, located in the mounting cavity, wherein light emitted by the infrared light module is capable of passing through the light-transmitting shell;

wherein the light-transmitting shell is integrally formed as a one-piece structure and comprises a light-transmitting portion and a bearing bracket, the bearing bracket being located at a central portion of the light-transmitting shell and the light-transmitting portion surrounding the bearing bracket;

wherein the infrared light module is disposed on a rear side of the bearing bracket facing away from the second contact face; and wherein the thermoelectric unit is disposed on a front side of the bearing bracket and positioned between the heat-conducting contact member and the bearing bracket.

2. The infrared massage head according to claim 1, wherein at least one connecting gap is formed on the light-transmitting shell or the mounting shell, the heat-conducting contact member comprises a contact portion and at least one connecting portion arranged on the contact portion, the contact portion is arranged outside the mounting cavity, and a side of the contact portion facing away from the mounting cavity is the second contact face;

the at least one connecting portion passes through the at least one connecting gap to enter the mounting cavity, and the at least one connecting portion is bendably configured to enable the heat-conducting contact member to be fixed relative to the light-transmitting shell.

3. The infrared massage head according to claim 2, wherein the thermoelectric unit is a thermoelectric semiconductor sheet, the thermoelectric unit is sandwiched between the contact portion and the light-transmitting shell and is attached to a side of the heat-conducting contact member facing away from the second contact face.

4. The infrared massage head according to claim 2, wherein the contact portion is circular, the number of the at least one connecting portion is more than one, and the more than one connecting portion is distributed to surround a circumference of the contact portion;

the number of the at least one connecting gap is more than one, and the more than one connecting gap are formed corresponding to the more than one connecting portion.

5. The infrared massage head according to claim 2, wherein the at least one connecting portion extends from an edge of the contact portion, and each of the contact portion and the at least one connecting portion is made of a metal material.

6. The infrared massage head according to claim 2, wherein an outer wall of the mounting shell is roughly cylindrical in shape, the light-transmitting shell is roughly circular in shape, and the contact portion is circular in shape.

7. The infrared massage head according to claim 1, wherein the infrared light module comprises a light board and a plurality of light beads annularly distributed on the light board;

the light-transmitting portion is annular and defines a mounting hole, the bearing bracket is arranged in the mounting hole, the light board is fixed in the mounting cavity, the light beads are arranged corresponding to the light-transmitting portion, and the thermoelectric unit and the heat-conducting contact member are mounted to the bearing bracket.

8. The infrared massage head according to claim 7, wherein the light board is fixed to the bearing bracket.

9. The infrared massage head according to claim 7, wherein the light-transmitting portion is made of a translucent material.

10. The infrared massage head according to claim 1, wherein the infrared light module comprises a red light unit and a near-infrared light unit.

11. The infrared massage head according to claim 1, further comprising a control board, a battery, and a control button, the control board and the battery are both arranged in the mounting cavity and are both fixed to the mounting shell, a portion of the control button is exposed outside the mounting shell, and the control board is electrically connected to the battery, the control button, the thermoelectric unit, and the infrared light module.

12. The infrared massage head according to claim 11, wherein the control button comprises a first control key and a second control key, the first control key is associated with the thermoelectric unit, and the second control key is associated with the infrared light module.

* * * * *